US00PP19601P2

(12) United States Plant Patent
Kordes

(10) Patent No.: US PP19,601 P2
(45) Date of Patent: Dec. 30, 2008

(54) GROUND COVER ROSE PLANT NAMED 'KORSUPIGEL'

(50) Latin Name: *Rosa hybrida*
Varietal Denomination: KORsupigel

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/008,955

(22) Filed: Jan. 14, 2008

(51) Int. Cl.
*A01H 5/00* (2006.01)

(52) U.S. Cl. ..... Plt./145

(58) Field of Classification Search ..... Plt./145
See application file for complete search history.

(56) References Cited

PUBLICATIONS

2007/0819 European Union CVPO summary Jun. 15, 2007 European Union.*

* cited by examiner

*Primary Examiner*—Annette H Para

(57) ABSTRACT

A new and distinct variety of rose with long lasting, novel yellow flowers, and attractive foliage with good disease resistance. It exhibits spreading growth with abundant flowers. The new variety propagates well from cuttings and by grafting. This new and distinct variety has shown to be uniform and stable in the resulting generations from asexual propagation.

1 Drawing Sheet

CROSS REFERENCES AND FEDERAL R&D STATEMENT

There are no cross referenced or related applications. This variety was developed without the aid of any research grant.

Latin name of genus and species: The botanical classification of the new rose plant is *Rosa hybrida.*

Variety denomination: The denomination of the new variety is 'KORsupigel'.

BACKGROUND OF THE INVENTION

The new variety of rose plant of the present invention originated from a controlled crossing in a breeding program of two distinct parents during the summer of 1994. The crossing was between an 'un-named seedling' and an 'un-named seedling'.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORsupigel'.

SUMMARY OF THE INVENTION

The new rose plant may be distinguished from its seed parent, an un-named seedling, by the following combination of characteristics:

1. 'KORsupigel' has yellow flowers while the seed parent has light pink flowers, and
2. 'KORsupigel' is a recurrent bloomer while the seed parent is not.

The new rose plant may be distinguished from its pollen parent, an 'un-named seedling' by the following combination of characteristics:

1. 'KORsupigel' has a spreading growth habit while the pollen parent has an upright growth habit, and
2. 'KORsupigel' has yellow flowers while the pollen parent has dark yellow flowers.

The objective of the hybridization was to create a new and distinct rose plant with unique qualities, such as:

1. Compact and uniform growth and flowering; when grown as a plant from cuttings;
2. Abundant attractive, recurrent flowers;
3. Attractive and abundant foliage; and
3. Resistance to diseases encountered in landscapes and gardens.

This combination of qualities is not present in prior rose cultivars. These objectives have been substantially achieved and in that distinguish 'KORsupigel' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORsupigel' was selected in May, 1995 from the seedling beds to be asexually propagated for further evaluation. The first asexual propagation of 'KORsupigel' was done by budding to seedling understocks in July, 1995 at the inventor's nursery in Offenseth-Sparrieshoop, Germany.

This initial and other subsequent propagations conducted in controlled environments demonstrate that 'KORsupigel' reproduces true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'KORsupigel'. Specifically illustrated is: a flower bud, partially opened bloom, open bloom, floral parts, sepals, juvenile foliage, stem exhibiting thorns, and leaves.

DETAILED BOTANICAL DESCRIPTION

The following is a description of 'KORsupigel', as observed growing in September, 2007 in a nursery in Jackson County, Oreg. plants of three years of age. Color references are made using The Royal Horticultural Society (London, England) Colour Chart, 2001 except where common terms of color are used.

For a comparison, several physical characteristics of the rose variety 'KORquelda', a rose variety from the same inventor described and illustrated in U.S. Plant Pat. No. 17,048 and issued on Aug. 22, 2006 are compared to 'KORsupigel' in Chart 1.

CHART 1

| Characteristic | 'KORsupigel' | 'KORquelda' |
|---|---|---|
| Overall height | 40-50 cm | 100-125 cm |
| Petal count | 40-60 | 40 |
| Average leaf size | 75 mm × 50 mm | 140 mm × 110 mm |

Parents:
- *Seed parent.*—An 'un-named seedling'.
- *Pollen parent.*—An 'un-named seedling'.

Classification:
- *Botanical classification.*—*Rosa hybrida,* 'KORsupigel'.
- *Commercial classification.*—Ground cover rose.

FLOWER AND FLOWER BUD

Blooming habit: Recurrent.

Flower bud:
- *Size.*—Upon opening, 16–20 mm in length from base of receptacle to end of bud and 14–18 mm diameter at its widest point.
- *Bud form.*—Short and globular.
- *Bud color.*—As sepals first unfold, bud color is Yellow Group 12B. When ¼ open, the upper surface of petals is Yellow Group 4B, and the lower surface is Yellow Group 4C. Guard petals are Yellow Group 12B with intonations of Yellow-Green Group 145A and Green-White Group 157C.
- *Sepals.*—Size: Average 18–20 mm long×7–8 mm wide. Shape: Sepals generally subulate. Sepal apex is generally cirrose. Foliaceous appendages not observed on sepal margins. Base is flat at union with receptacle. Quantity: Five. Margins: Stipitate glands present on 2 to 3 sepals per bud. Surface texture: Upper surface covered with fine white hairs. Lower surface is smooth. Stipitate glands are present. Color: Upper surface Yellow-Green Group 144C. Lower surface Yellow-Green Group 144B. Intonations of Yellow-Green 144D present.

Receptacle:
- *Surface.*—Smooth.
- *Color.*—Green Group 143C.
- *Shape.*—Funnel.
- *Size.*—5–7mm(h)×7–8 mm (w).

Peduncle:
- *Surface.*—With fine immature prickles and stipitate glands.
- *Length.*—30–35 mm average length.
- *Diameter.*—1.0–1.5 mm average diameter.
- *Color.*—Yellow-Green Group 145B.
- *Strength.*—Somewhat strong.
- *Borne.*—Multiple flower buds per stem, generally 4 to 6.

Flower bloom:
- *Fragrance.*—Light.
- *Duration.*—On the plant 2–4 days. Senesced petals drop away cleanly.
- *Size.*—*Medium flowered garden rose. When open, the average flower diameter is* 50–60 mm and the average flower height is 27 mm.
- *Form.*—Shape of flower when viewed from the side: Upon opening, upper part: Flat. Upon opening, lower part: Flattened convex. Open flower, upper part: Flat. Open flower, lower part: Concave.

Color:
- *Upon opening, petals.*—Outermost petals: Outer Side: Yellow Group 12C. Inner Side: Yellow Group 12B. Innermost petals: Outer Side: Yellow Group 12A. Inner Side: Yellow Group 12A.
- *Upon opening, basal petal spots.*—No distinctive coloration at petal base observed.
- *After opening, petals.*—Outermost petals: Outer Side: Yellow Group 11C. Inner Side: Yellow Group 11B. Innermost petals: Outer Side: Yellow Group 10C. Inner Side: Yellow Group 10C.
- *After opening, basal petal spots.*—Basal petal spot, outermost petals: Outer Side: Yellow Group 11A. Inner Side: Yellow Group 11A. Basal petal spot, innermost petals: Outer Side: Yellow Group 11A. Inner Side: Yellow Group 11A. Variegations: Occasional greenish streak on the guard petals with intonations of Yellow-Green Group 145A and Green-White Group 157C.

General tonality: On open flower Yellow Group 10B. No change in the general tonality at the end of the 5th day. Afterwards, general tonality is Yellow Group 5D.

Petals:
- *Petal count.*—Approximately 40–60 petals under normal conditions.
- *Petal reflex.*—Petals reflex slightly.
- *Petal edge.*—With point in center of margin.
- *Petal shape.*—Deltoid. Apex shape is round. Shape of base is acute.
- *Petal Size.*—25–30 mm long; 15–20 mm wide.
- *Thickness.*—Thin.
- *Petal arrangement.*—Generally in a regular pattern with overlapping edges.

Petaloids: Present.
- *Petaloid count.*—Average of 10–15 per flower.
- *Petaloid edge.*—With point in center of margin.
- *Petaloid texture.*—Smooth.
- *Petaloid shape.*—Cuneate to obovate.
- *Petaloid size.*—Petaloids are 8–10 mm long and 5–10 mm wide.
- *Petaloid color.*—Color of inner side is Yellow Group 11B. Color of outer side is Yellow Group 11B.

Reproductive organs:
- *Pistils.*—Approximately 30–40 present. Stigmas: Location: Slightly superior in position to anthers. Color: Yellow-Green Group 154C. Styles: Length: 6–7 mm long. Color: Yellow-Green Group 154C.
- *Stamens.*—Approximately 20–30 on average and regularly arranged. Anthers: Size: 1.5–2.0 mm long.

Color: Yellow-Orange Group 20A. Pollen: Absent. Filaments: Color: Yellow Group 2A. Length: 5–6 mm.

THE PLANT

Plant growth: Vigorous. Spreading habit. When grown as a budded nursery plant the average plant height is 40 cm and the average plant width is 60 cm.

Stems:

*Stem color.*—Young wood: Yellow-Green Group 146D. Older wood: Yellow-Green Group 146D.

*Stem surface.*—Young wood: Smooth. Older wood: Smooth.

Prickles: Present.

*Incidence.*—10–15 per 10 cm of stem.

*Size.*—Average length: 7–9 mm.

*Color.*—Immature prickles: Greyed-Yellow Group 160C. Mature prickles: Greyed-Yellow Group 162C. Senescing to Greyed-Orange Group 164A.

*Shape.*—Immature prickles: Linear Mature prickles: Deeply concave to linear.

*Anthocyanin.*—Color: Greyed-Purple Group 184B.

Leaves and leaflets: Normally 5–7 leaflets on normal leaves in middle of the stem.

*Leaf size.*—75 mm (1)×50 mm (w).

*Quantity.*—Abundant.

*Texture.*—Upper side of leaflet: Glossy and smooth. Under side of leaflet: Matte and rough.

*Color, mature foliage.*—Upper Leaf Surface: Green Group 137A. Lower Leaf Surface: Yellow-Green Group 146B.

*Color, juvenile foliage.*—Upper Leaf Surface: Green Group 138A. Lower Leaf Surface: Yellow-Green Group 146C.

*Anthocyanin intonation.*—Present. Location: Intonations present on juvenile leaf margins. Color: Greyed-Purple Group 183B.

Stipules:

*Size.*—10–15 mm long. 6–7 mm between the tips of the stipule. Main body of stipule 5 mm in width.

*Shape.*—Longitudinally flanged. Inverted at base. Winged at apex.

*Stipule color.*—Green Group 138A. Anthocyanin color is Greyed-Red Group 181B.

*Presence of stipitate glands.*—Present on margins.

*Margins.*—Serrated.

Petiole:

*Length.*—5–10 mm.

*Diameter.*—1.0–1.5 mm.

*Petiole color.*—Green Group 138A. Anthocyanin present on juvenile tissue. Color: Greyed Purple Group 183B.

*Underneath.*—A few small prickles underneath.

*Stipitate glands.*—Stipitate glands present on margins.

Petiole rachis:

*Length.*—10–15 mm.

*Diameter.*—1.0–1.5 mm.

*Color.*—Green Group 138A. Anthocyanin present on juvenile tissue. Color: Greyed-Purple Group 183B.

*Margins.*——*Stipitate glands present on margins.*

*Prickles.*—A few small prickles underneath.

*Stipitate glands.*—Limited numbers of stipitate glands on margins.

Leaflets:

*Size.*—Average size of the terminal leaflet is 25–30 mm (1)×18–22 mm (w).

*Shape.*—Obtuse. Base: Ovate. Apex: Acute.

*Margins.*—Serrated.

*Texture.*—Thin and leathery.

Hips/Seed formation: None observed.

Winter hardiness: To date, the variety has been grown successfully in Zone 5.

Disease resistance: Above average resistance to powdery mildew, rust, Black spot disease under normal growing conditions.

I claim:

1. A new and distinct variety of rose plant characterized by the following combination of characteristics:

(a) Forms attractive, long lasting yellow flowers;

(b) Exhibits spreading growth habit;

(c) Propagates well using traditional methods, and;

(d) Exhibits very good resistance to disease under normal growing conditions, substantially as herein illustrated and described.

* * * * *

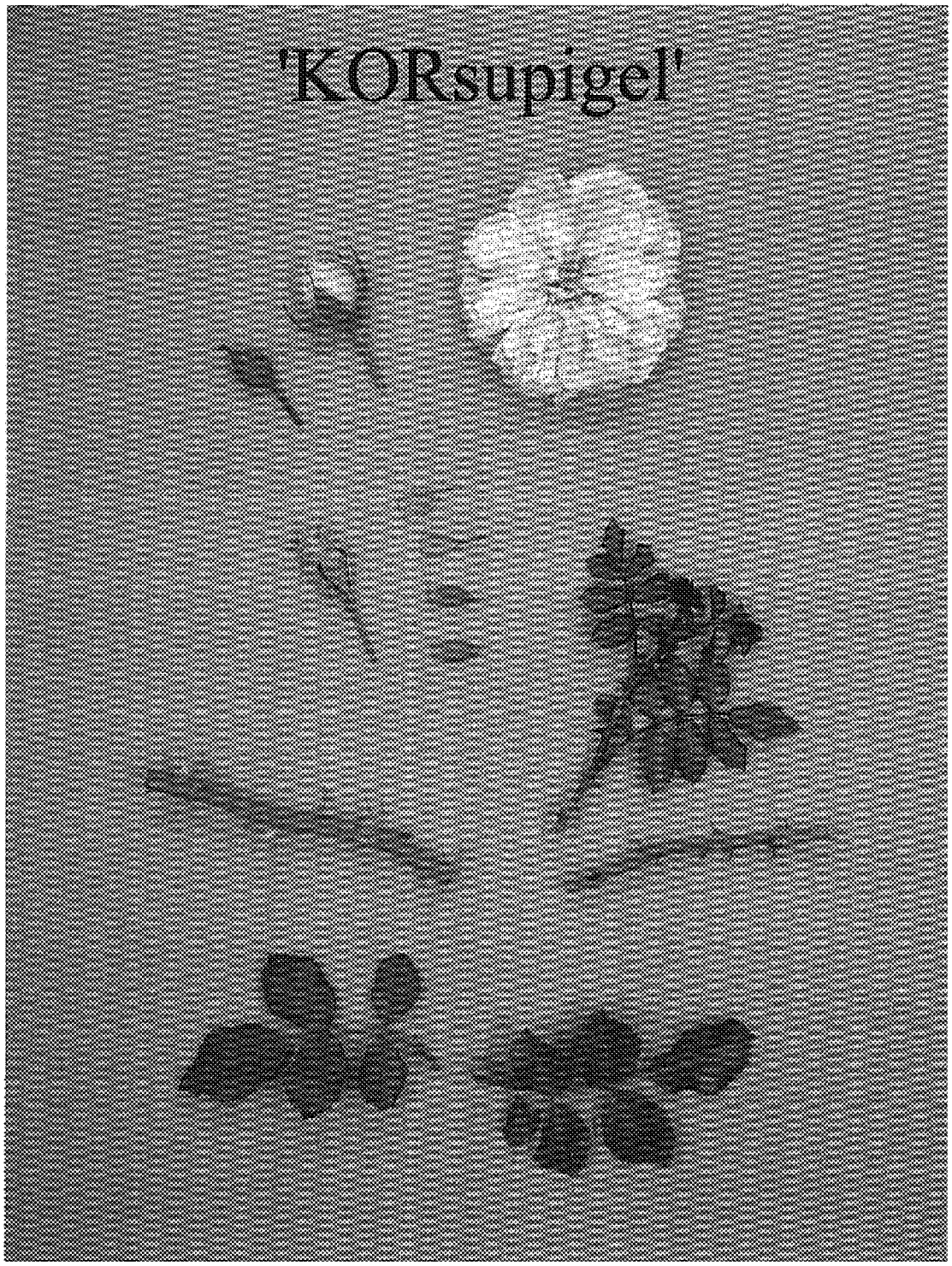
'KORsupigel'